United States Patent [19]

Yamada et al.

[11] 4,046,904
[45] Sept. 6, 1977

[54] NOVEL PENICILLIN, AND ITS PREPARATION AND USE

[75] Inventors: Hirotada Yamada, Nishinomiya; Hisao Tobiki, Kobe; Norihiko Tanno, Takarazuka; Kozo Shimago, Toyonaka; Kosaku Okamura, Minoo; Takenari Nakagome, Nishinomiya; Toshiaki Komatsu, Takarazuka; Akio Izawa, Kawanishi; Hiroshi Noguchi, Nishinomiya; Kenji Irie, Takarazuka; Yasuko Eda, Toyonaka, all of Japan

[73] Assignee: Sumitomo Chemical Company, Limited, Japan

[21] Appl. No.: 658,035

[22] Filed: Feb. 13, 1976

[30] Foreign Application Priority Data

Feb. 14, 1975 Japan .................. 50-19040

[51] Int. Cl.² ............ A61K 31/43; C07D 499/68
[52] U.S. Cl. ............................. 424/271; 260/239.1
[58] Field of Search .................. 260/239.1; 424/271

[56] References Cited

U.S. PATENT DOCUMENTS 3,864,329  2/1975  Tobiki et al. .................. 260/239.1
3,945,995  3/1976  Yamada et al. ................ 260/239.1
3,954,733  5/1976  Tobiki et al. .................. 260/239.1

*Primary Examiner*—Gerald A. Schwartz
*Attorney, Agent, or Firm*—Birch, Stewart, Kolasch and Birch

[57] ABSTRACT

A penicillin of the formula:

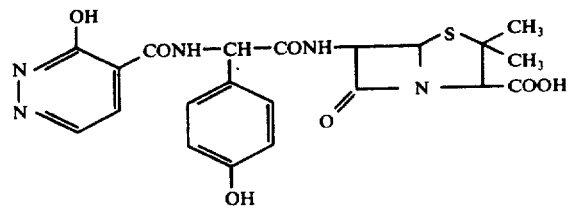

(i.e. 6-[D-2-(3-hydroxypyridazine-4-carbonamido)-2-(p-hydroxyphenyl)acetamido]penicillanic acid), which is valuable as an antibacterial agent, a nutritional supplement in animal feeds and a therapeutic agent in poultry and mammals including man and is especially useful in the treatment of infectious diseases caused by Gram-positive and Gram-negative bacteria.

3 Claims, No Drawings

NOVEL PENICILLIN, AND ITS PREPARATION AND USE

The present invention relates to 6-[D-2-(3-hydroxypyridazine-4-carbonamido)-2-(p-hydroxyphenyl)acetamido]penicillanic acid, and its preparation and use.

The said 6-[D-2-(3-hydroxypyridazine-4-carbonamido)-2-(p-hydroxyphenyl)acetamido]penicillanic acid is representable by the formula:

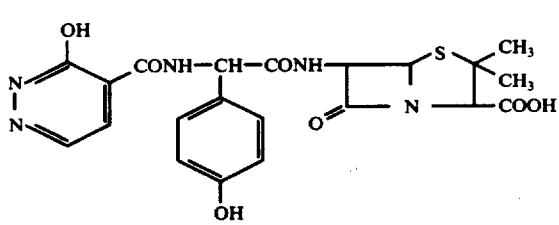

(I)

It is well known that "Ampicillin" is highly effective in treatment of infections caused by Gram-positive and Gram-negative bacteria but does not exert any appreciable anti-Pseudomonas activity. For the treatment of infections with Pseudomonas, some synthetic penicillins such as "Carbenicillin" and "Sulfocillin" have been used in recent years, but their anti-Pseudomonas activity is not sufficiently strong. In U.S. Pat. No. 3,864,329, Japanese Patent Publication (unexamined) No. 92391/1973 and German Patent (Offen.) No. 2,362,279, there have been disclosed some penicillins with good antibacterial activity against Gram-positive and Gram-negative bacteria including Pseudomonas.

As the result of an extensive study, it has been found that 6-[D-2-(3-hydroxypyridazine-4-carbonamido)-2-(p-hydroxyphenyl)acetamido]penicillanic acid shows a strong antibacterial activity with most desirable and practical pharmaceutical properties and is a particularly useful antibacterial agent.

Although the compound of the present invention is similar in structure to the penicillins disclosed in the said patents, its antibacterial activity in vitro and in vivo is much stronger and its pharmacokinetic properties are more desirable than these of said penicillins. For example, the compound of the present invention exerts much stronger antibacterial activity in vitro and in vivo against various pathogenic organisms than 6-[D-2-(4-hydroxypyridine-3-carbonamido)-2-(p-hydroxyphenyl)acetamido]penicillanic acid and 6-[D-2-(3-hydroxypyridazine-4-carbonamido)-2-phenylacetamido]penicillanic acid, which are disclosed in the said Japanese Patent Publication. The compound of the present invention also shows lower toxicity, broader antibacterial spectra, higher serum concentrations, higher urinary excretion rate, lower protein-binding ratio, weaker pain when administered parenterally, and higher solubility in pharmaceutical diluents (e.g. water).

Thus, the present invention provides 6-[D-2-(3-hydroxypyridazine-4-carbonamido)-2-(p-hydroxyphenyl)acetamido]penicillanic acid and its non-toxic, pharmaceutically acceptable salts, which are valuable as antibacterial agents, nutritional supplements in animal feeds and therapeutic agents in poultry and mammals including man, particularly in treatment of infectious diseases caused by Gram-positive and Gram-negative bacteria.

The non-toxic, pharmaceutically acceptable salts are, for instance, the inorganic salts such as sodium, potassium, ammonium, calcium and magnesium salts and the organic salts such as diethylamine, triethylamine, N,N'-dibenzylethylenediamine, diethanolamine, pyrrolidine, morpholine, procain, L-arginine and L-lysine salts.

The compound of the present invention can be prepared according to a per se conventional method, for example, as shown in the following reaction scheme:

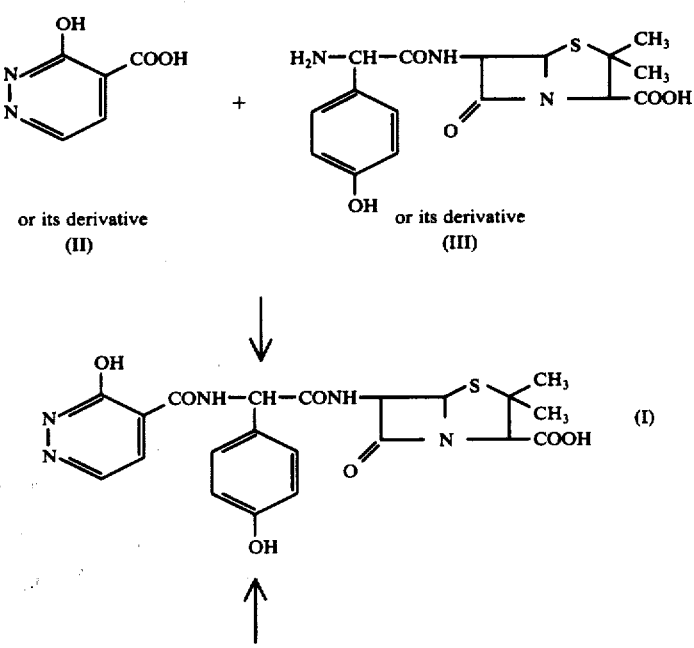

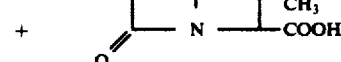

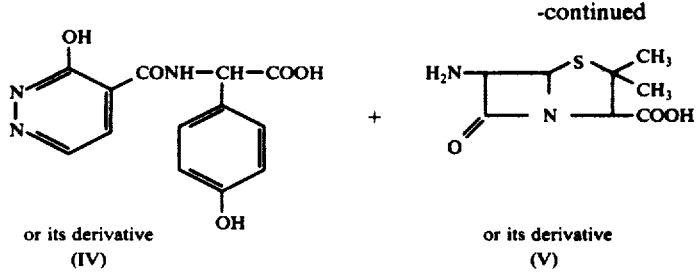

or its derivative
(IV)

or its derivative
(V)

The reaction between the carboxylic acid (II) or its derivative and the amine (III) or its derivative is usually carried out in an inert solvent such as a polar solvent (e.g. dichloromethane, chloroform, acetone, tetrahydrofuran, dioxane, acetonitrile, methylisobutylketone, ethanol, dimethylformamide, dimethylacetamide, dimethylsulfoxide, sulfone, hexamethylphosphoric triamide, water), a non-polar solvent (e.g. benzene, toluene, petroleum ether, n-hexane) or their mixture. In some cases, there may be used an aqueous medium. The reaction temperature is not limitative and may be usually below 50° C.

As the derivative of the carboxylic acid (II) on the carboxyl group, there are included halides, acid anhydrides, mixed acid anhydrides, acid azolides, acid azides, active esters, etc. Examples of the acid azolides are those prepared from imidazole, substituted imidazole, dimethylpyrazole, triazole, tetrazole, etc. The active esters may be cyanomethyl ester, p-nitrophenyl ester, 2,4-dinitrophenyl ester, trichlorophenyl ester, pentachlorophenyl ester, methanesulfonyl ester, 1-hydroxy-2(1H)-pyridone, N-hydroxysuccinimide, N-hydroxydiphthalimide, etc.

When the carboxylic acid (II) is used in the form of a free acid, the amidation with the amine (III) or its derivative can preferably be carried out in the presence of a coupling reagent such as N,N'-dicyclohexylcarbodiimide, N-cyclohexyl-N'-morpholinoethylcarbodiimide, triphenylphosphine, 2-ethyl-5-(m-sulfonyl)-isoxazolium hydroxide inner salt or carbonyldiimidazole.

When the mixed acid anhydride is prepared for activation of the carboxylic acid (II), the following procedure may be recommended. Thus, 1 molar amount of the carboxylic acid (II) is reacted with about 2 molar amount of a lower alkoxycarbonyl halide (e.g. ethyl chloroformate, isobutyl chloroformate) or a lower alkanoyl halide (e.g. pivaloyl chloride) in the presence of about 2 molar amount of a base to give a mixed acid anhydride of the formula:

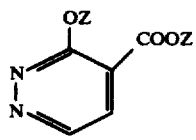

(II')

wherein Z is acyl or lower alkoxycarbonyl.

The product in the amidation using such mixed anhydride is the one representable by the formula:

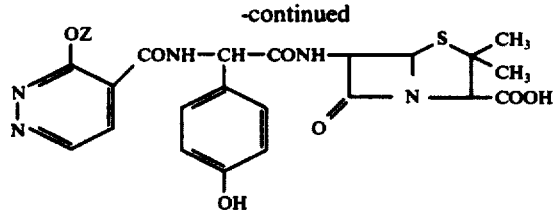

(I')

wherein Z is as defined above, which may be converted into the penicillin (I) by treatment with an organic or inorganic base (e.g. sodium carbonate, potassium carbonate, sodium hydroxide, ammonia water, triethylamine, dimethylamine, potassium 2-ethylhexanoate). The conversion can be also accomplished in acidic conditions, although basic conditions are usually preferred.

The derivative of the amine (III) may be, for example, salts, esters or N-substituted compounds thereof. Examples of the salts are salts of alkali metals (e.g. sodium, potassium), alkaline earth metals (e.g. calcium, barium), organic bases (e.g. trimethylamine, triethylamine) and organic sulfonic acids (e.g. toluenesulfonic acid, naphthalenesulfonic acid, tetrahydronaphthalenesulfonic acid). Examples of the esters and the N-substituted compounds are as follows:

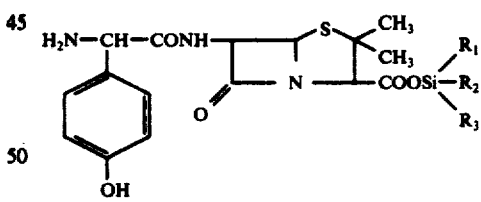

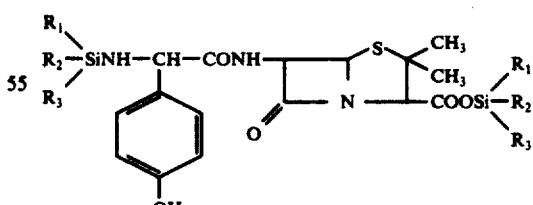

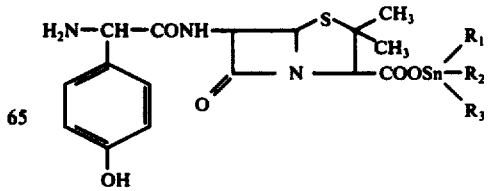

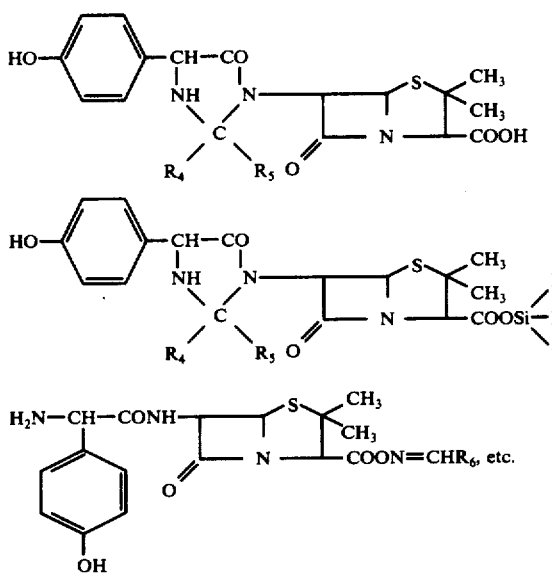

wherein $R_1$, $R_2$ and $R_3$ are each lower alkyl or lower alkoxy, $R_4$ and $R_5$ are each lower alkyl and $R_6$ is lower alkyl, aryl or a hetero ring.

Further examples of the ester unit in the esters of the amine (III) are as follows: toluenesulfonylethyl ester, p-nitrobenzyl ester, benzyl ester, phenacyl ester, diphenylmethyl ester, substituted diphenylmethyl ester, trityl ester, benzoyloxymethyl ester, lower alkanoyloxymethyl ester, dimethylmethyleneamino ester, p-nitrophenyl ester, methylsulfonylphenyl ester, methylthiophenyl ester, t-butyl ester, 3,5-di-t-butyl-4-hydroxybenzyl ester, trichloroethyl ester, etc. These ester units are all conventionally employed as a group protecting a carboxylic acid radical in the related art field. These esters may be employed in the salt form such as those obtained by the use of organic sulfonic acids (e.g. toluenesulfonic acid, tetrahydronaphthalenesulfonic acid).

After the amidation with the carboxylic acid (II) or its derivative, these ester parts can be eliminated using a per se conventional procedure such as reduction or hydrolysis under conditions so mild as not to affect the β-lactam ring of the penicillin nucleus.

The reaction between the carboxylic acid (IV) or its derivative and the amine (V) or its derivative may be carried out in the similar manner to that between the carboxylic acid (II) or its derivative and the amine (III) or its derivative as explained above.

In treatment of infections in mammals, the compound of the present invention can be administered through various routes such as intramuscular or intravenous injection or instillation at a daily dose of 300 mg to 20 g in divided dosages, e.g. three or four times a day.

The compound of the present invention can be made up to a conventional dosage unit form (e.g. solutions, dispersions, emulsions, powders, tablets, capsules, etc.) in the manner known per se.

The following examples are given to illustrate the invention more precisely without limiting it thereto.

EXAMPLE 1

To a solution of 8.0 g of 6-(D-α-amino-α-p-hydroxyphenylacetamido)penicillanic acid trihydrate and 2.02 g of triethylamine in 40 ml of dimethylformamide were added 5.48 g of p-nitrophenyl 3-hydroxypyridazine-4-carboxylate while stirring at room temperature, and stirring was continued at the same temperature for 40 minutes. After addition of 3.16 g of sodium 2-ethylhexanoate to the reaction mixture, stirring was further continued for 15 minutes. A small amount of undissolved materials was eliminated by filtration, and the filtrate was admixed with 200 ml of dichloromethane and 200 ml of acetone. The precipitated crystals were collected by filtration, washed successively with dichloromethane, acetone and ether and dried over phosphorus pentoxide under reduced pressure to give 9.0 g of the sodium salt of 6-[D-2-(3-hydroxypyridazine-4-carbonamido)-2-(p-hydroxyphenyl)acetamido]penicillanic acid. M.P. 218° – 220° C (decomp.).

EXAMPLE 2

6-[D-2-(3-Hydroxypyridazine-4-carbonamido)-2-(p-hydroxyphenyl)acetamido]penicillanic acid (sodium salt) (100 - 200 mg) in powder form is aseptically admitted into a glass ampoule, which is then sealed. Upon use, the penicillin is dissolved in an appropriate amount of sterilized water containing no pyrogenic substance, and the resulting solution is injectionally administered.

The antibacterial activity in vitro and in vivo of 6-[D-2-(3-hydroxypyridazine-4-carbonamido-2-(p-hydroxyphenyl)acetamido]penicillanic acid (hereinafter referred to as "Compound (I)") against several organisms was compared with two typical and representative penicillins disclosed in Japanese Patent Publication (unexamined) No. 92391/1973, i.e. 6-[D-2-(4-hydroxypyridine-3-carbonamido)-2-(p-hydroxyphenyl)acetamido]penicillanic acid (hereinafter referred to as "Compound (A)"):

(A)

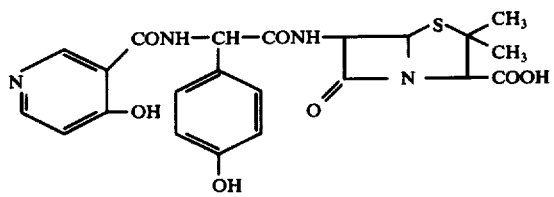

and 6-[D-2-(3-hydroxypyridine-4-carbonamido)-2-phenylacetamido]penicillanic acid (hereinafter referred to as "Compound (B)"):

(B)

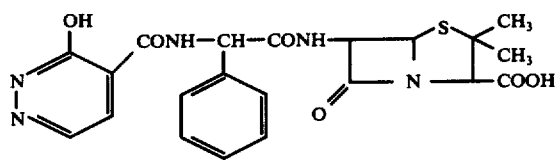

The median minimum inhibitory concentrations obtained with Compound (I) and Compound (A) against 170 bacterial isolates from hospital patients representing eight genera are shown in Table 1, which demonstrates that the antibacterial activity of Compound (I) is superior to that of Compound (A), especially against organisms such as *Klebsiella pneumoniae, Proteus vulgaris, Proteus morganii, Enterobacter aerogenes* and *Serratia.*

Table 1

| Organism | Number of clinical isolates | Median minimum inhibitory concentration (μg/ml) | |
|---|---|---|---|
| | | Compound (I) | Compound (A) |
| Staphylococcus aureus | 37 | 13 | 21 |
| Escherichia | 23 | 12 | 14 |
| Klebsiella pneumoniae | 26 | 21 | 73 |
| Proteus vulgaris | 7 | 8.8 | 115 |
| Proteus morganii | 14 | 4.4 | 50 |
| Enterobacter aerogenes | 8 | 25 | 100 |
| Serratia | 6 | 31 | >200 |
| Pseudomonas aeruginosa | 49 | 10 | 5 |

Note: Compound (I) and Compound (A) were subjected to the test in the form of the sodium salt. The minimum inhibitory concentration (MIC) was determined using the agar-plate dilution method recommended by Japan Society of Chemotherapy.

The relative activities of Compound (I), Compound (A) and Compound (B) against various intraperitoneal infections in mice evaluated by the minimum inhibitory concentrations and the mean median protective doses (subcutaneously administered) are shown in Table 2, from which it is understood that the $PD_{50}$ values of Compound (I) are markedly superior to those of Compound (A) and Compound (B), especially against organisms such as *Klebsiella pneumoniae* and *Pseudomonas aeruginosa*.

Table 2

| Organism | Strain No. | MIC (μg/ml) | | | $PD_{50}$ (mg/kg) | | |
|---|---|---|---|---|---|---|---|
| | | Compound (I) | Compound (A) | Compound (B) | Compound (I) | Compound (A) | Compound (B) |
| Eshcerichia coli | 37 | 12.5 | 12.5 | 12.5 | 31 | — | 57 |
| Escherichia coli | NIHJ | 6.25 | 12.5 | 12.5 | 3.2 | 3.0 | — |
| Klebsiella pneumoniae | 20 | 12.5 | 100 | 12.5 | 31 | >150 | 71 |
| Klebsiella pneumoniae | 6 | 25 | 100 | 25 | 36 | 120 | 50 |
| Klebsiella pneumoniae | 1 | 6.25 | 3.13 | 12.5 | 25 | 100 | — |
| Pseudomonas aeruginosa | T | 25 | 12.5 | 12.5 | 35 | 51 | 160 |
| Pseudomonas aeruginosa | NC-5 | 12.5 | 6.25 | 12.5 | 22 | 60 | 180 |

Note: Compound (I), Compound (A) and Compound (B) were subjected to the test in the form of the sodium salt. For each test, eight male ICR-SLC strain mice were used at each dose level. MIC was determined by the nutrient broth dilution method. In determination of $PD_{50}$, subcutaneous treatment was carried out twice, i.e. 1 and 4 hours after infection.

Then, the antibacterial activity in vitro and in vivo of Compound (I) against several organisms and the pharmacokinetic profiles of Compound (I) were compared with those of a typical and representative compound disclosed in German Patent (Offen.) No. 2,362,279, i.e. 6-[D-2-(4-hydroxy-1,5-naphthyridine-3-carbonamido)-2-(p-hydroxyphenyl)acetamido]penicillanic acid (hereinafter referred to as "Compound (C)") of the formula:

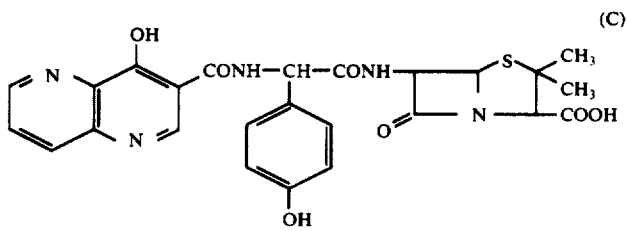

The minimum inhibitory concentrations obtained with Compound (I) and Compound (C) against the following organisms representing 6 genera are shown in Table 3.

Table 3

| Organism | Strain No. | MIC (μg/ml) | |
|---|---|---|---|
| | | Compound (I) | Compound (C) |
| Staphylocossuc aureus | 209P | 0.39 | 0.78 |
| Escherichia coli | NIHJ | 6.25 | 1.56 |
| Proteus miravilis | GN2425 | 6.25 | 1.56 |
| Proteus vulgaris | HX19 | 0.025 | 0.025 |
| Klebsiella pneumoniae | PCI602 | 12.5 | 12.5 |
| Pseudomonas aeruginosa | 104 | 1.56 | 1.56 |

Note: Compound (I) and Compound (C) were subjected to the test in the form of the sodium salt.

It is understood from Table 3 that the antibacterial activity of Compound (I) is superior to that of Compound (C) against organisms such as *Staphylococcus aureus* but inferior against organisms such as *Escherichia coli* and *Proteus mirabilis*.

The median minimum inhibitory concentrations obtained with Compound (I) and Compound (C) against 60 bacterial isolates from hospital patients representing 2 genera are shown in Table 4, which demonstrates that the antibacterial activity of Compound (I) is superior to that of Compound (C) against organisms such as *Staphylococcus aureus* and *Streptococcus faecalis*.

Table 4

| Organism | Number of Strains | Median minimum inhibitory concentration (μg/ml) | |
|---|---|---|---|
| | | Compound (I) | Compound (C) |
| Staphylococcus aureus | 37 | 15 | 60 |
| Streptococcus | 23 | 2.0 | 3.8 |

Table 4-continued

| Organism | Number of Strains | Median minimum inhibitory concentration (μg/ml) | |
|---|---|---|---|
| | | Compound (I) | Compound (C) |
| faecalis | | | |

Note: Compound (I) and Compound (C) were subjected to the test in the form of the sodium salt. MIC was determined using the agar-plate dilution method.

The relative activities of Compound (I) and Compound (C) against various intraperitioneal infections in mice evaluated by the minimum inhibitory concentrations and the means median protective doses (subcutaneously administered) are shown in Table 5.

Table 5

| Organism | Strain No. | MIC (μg/ml) | | PD$_{50}$ (mg/kg) | |
|---|---|---|---|---|---|
| | | Compound (I) | Compound (C) | Compound (I) | Compound (C) |
| Staphylococcus aureus | A24 | 0.39 | 1.56 | 2.0 | 32 |
| Streptococcus faecalis | F10 | 1.56 | 1.56 | 1.1 | 6 |
| Klebsiella pneumoniae | 1 | 6.25 | 6.25 | 16 | 18 |
| Pseudomonas aeruginosa | TS | 6.25 | 3.13 | 22 | 15 |

Note: Compound (I) and Compound (C) were subjected to the test in the form of the sodium salt. For each test, five male ICR-SLC strain mice were used at each dose level. MIC was determined by the nutrient broth dilution method. In determination of PD$_{50}$, subsutaneous treatment was carried out three times, i.e. 1, 3 and 5 hours after infection.

It is understood from Table 5 that the PD$_{50}$ values of Compound (I) are markedly superior to those of Compound (C) against organisms such as *Staphylococcus aureus* and *Streptococcus faecalis* and approximately equal against *Klebsiella pneumoniae*, but against *Pseudomonas aeruginosa*, the PD$_{50}$ value of Compound (I) is inferior to that of Compound (C).

The following data are related to the pharmacokinetic profiles of Compound (I) compared with Compound (C). Thus, the protein-binding rates in human serum of Compound (I) and Compound (C) are given in Table 6, from which it is seen that Compound (I) has a lower protein-binding rate than Compound (C), and the former is less inactivated in serum when administered.

Table 6

| Compound | Binding rate with human serum (%) | |
|---|---|---|
| | Ultrafiltration method | Ultracentrifugation method |
| (I) | 58 | 60 |
| (C) | 90 | 92 |

Note: Compound (I) and Compound (C) were subjected to the test in the form of the sodium salt.

The peak serum concentrations of Compound (I) and Compound (C) in ICR strain mice following subcutaneous administration at 50 mg/kg are shown in Table 7.

Table 7

| Compound | Serum level (μg/ml) | | | |
|---|---|---|---|---|
| | ¼ hr. | ½ hr. | 1 hr. | 2 hr. |
| (I) | 69 | 35 | 14 | 3 |
| (C) | 44 | 32 | 8 | 5 |

Note: Compound (I) and Compound (C) were subjected to the test in the form of the sodium salt. For the test, three male ICR-SLC strain mice were used. The bioassay was carried out according to the disc method using *Bacillus subtilis*.

The urinary excretion rates of Compound (I) and Compound (C) following an intramuscular administration of 20 mg/kg in male Wistar-HLA strain rats are shown in Table 8.

Table 8

| Compound | Urinary excretion rate (%) | | |
|---|---|---|---|
| | 0-6 hr. | 6-24 hr. | 0-24 hr. |
| (I) | 54 | 1.0 | 55 |
| (C) | 19.5 | 0.5 | 20 |

Note: Compound (I) and Compound (C) were subjected to the test in the form of the sodium salt.

The acute toxicity of Compound (I) and Compound (C) in ICR strain mice when administered by intraperitoneal route are shown in Table 9.

Table 9

| Compound | LD$_{50}$ (mg/kg) |
|---|---|
| (I) | 7100 |
| (C) | 3100 |

Note: Compound (I) and Compound (C) were subjected to the test in the form of the sodium salt.

From the above results, it is understood that Compound (I) has excellent features as a chemotherapeutic agent. Higher serum level and higher urinary recovery rate of Compound (I) promise higher protection in the treatment of various infectious diseases including urinary tract infections caused by Gram-positive and Gram-negative bacteria.

What is claimed is:

1. A compound of the formula:

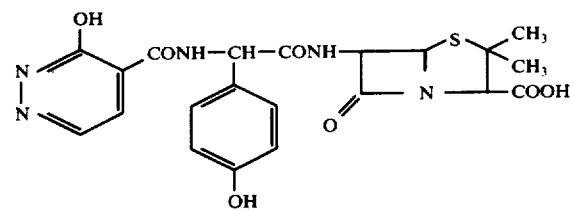

or a non-toxic, pharmaceutically acceptable salt thereof.

2. An antibacterial composition containing an antibacterially effective amount of 6-[D-2-(3-hydroxypyridazine-4-carbonamido)-2-(p-hydroxyphenyl)acetamido]-penicillanic acid or a non-toxic, pharmaceutically acceptable salt thereof and a pharmaceutically acceptable carrier or diluent.

3. A method of treating bacterial infection which comprises administering to a human being or animal an antibacterially effective amount of 6-[D-2-(3-hydroxypyridazine-4-carbonamido)-2-(p-hydroxyphenyl)acetamido]penicillanic acid or a non-toxic, pharmaceutically acceptable salt thereof.

* * * * *